United States Patent
Mizutani

[19]

[11] Patent Number: 5,772,650
[45] Date of Patent: Jun. 30, 1998

[54] ABSORBENT SANITARY ARTICLE INCLUDING WINGS

[75] Inventor: Satoshi Mizutani, Kawanoe, Japan

[73] Assignee: Uni-Charm Corporation, Ehime-ken, Japan

[21] Appl. No.: 439,559

[22] Filed: May 11, 1995

[30] Foreign Application Priority Data

May 13, 1994 [JP] Japan ................................ 6-100163

[51] Int. Cl.[6] .................................................. A61F 13/15
[52] U.S. Cl. ............................................ 604/387; 604/386
[58] Field of Search ............................ 604/385.1, 386, 604/387

[56] References Cited

U.S. PATENT DOCUMENTS

| | | | |
|---|---|---|---|
| 4,419,994 | 12/1983 | Hilton | 128/206.19 |
| 4,589,876 | 5/1986 | Van Tilburg | 604/385.1 |
| 4,687,478 | 8/1987 | Van Tilburg | |
| 5,275,591 | 1/1994 | Mavinkurve | 604/387 |
| 5,387,210 | 2/1995 | Murakami | 604/385.1 |
| 5,423,786 | 6/1995 | Fung et al. | 604/360 |
| 5,429,630 | 7/1995 | Beal et al. | 604/385.1 |
| 5,490,847 | 2/1996 | Correa et al. | 604/385.1 |

FOREIGN PATENT DOCUMENTS

| | | |
|---|---|---|
| A-0-134086 | 3/1985 | European Pat. Off. . |
| A-0575611 | 1/1992 | European Pat. Off. . |
| 2214085 | 8/1989 | United Kingdom . |
| 2270001 | 2/1994 | United Kingdom . |

Primary Examiner—Mark O. Polutta
Attorney, Agent, or Firm—Lowe, Price, LeBlanc & Becker

[57] ABSTRACT

An improved sanitary article such as a menstruation pad, sanitary napkin and the like having a pair of wings, wherein each of the wings includes a composite sheet comprising a nonwoven fabric striped with strips of plastic film substantially extending longitudinally of said article and bonded to the upper surface of said nonwoven fabric.

5 Claims, 4 Drawing Sheets

ABSORBENT SANITARY ARTICLE INCLUDING WINGS

BACKGROUND OF THE INVENTION

The present invention relates to an absorbent sanitary article such as a menstruation pad, sanitary napkin and the like having a pair of wings extending outward from transversely opposite sides thereof.

Menstruation pads having a pair of wings extending outward from transversely opposite sides thereof are well known. These wings are provided in order to fasten the pad to the crotch zone of the wearer's shorts and at the same time to prevent transversely opposite side edges of the crotch zone from being smeared with menstrual discharge. To achieve these effects, it is well known to attach the wings to their lower surfaces with adhesive zones, respectively, so that the wings may be adhesively fixed to the crotch zone of the wearer's shorts on its lower surface by folding the respective wings along the side edges of the crotch zone back to the lower surface of the crotch zone. The pad of this type is disclosed, for example, in U.S. Pat. No. 4,687,478.

The pad having such wings is supplied to a consumer usually in a form such that the wings are folded along their base ends back onto the upper or lower surface of the pad, then this assembly is folded longitudinally in two or three and individually packaged in an envelope. Consequently, the pad has fold traces both in length and width and sometimes the wings also may include such fold traces. Such fold traces, if included by the wings, will inconveniently prevent the wings from being folded accurately along the crotch zone's side edges of the wearer's shorts and likely cause the wings to be folded along lines which are remote from said side edges. In this case, the pad may be unstable or gaps may be left between the wings and the respective side edges of the wearer's shorts, although the wearer takes it for granted that the pad was reliably fastened to the shorts by means of the wings. As a result, menstrual discharge may flow into said gaps and the shorts may be smeared therewith.

Accordingly, it is a principal object of the invention to solve the above-mentioned problem by providing at least a portion of each wing with a composite sheet comprising a nonwoven fabric striped with plurality of strips of plastic film bonded to the nonwoven fabric.

SUMMARY OF THE INVENTION

The object set forth above is achieved, according to the invention, by an absorbent sanitary article such as menstruation pad having a basic body comprising a liquid-permeable topsheet, a liquid-impermeable backsheet and a liquid-absorbent core disposed between these two sheets, and a pair of wings extending outward from transversely opposite sides of said basic body, wherein each of said wings is at least partially made of a composite sheet comprising a nonwoven fabric striped with strips of plastic film substantially extending longitudinally of said article and bonded to the upper surface of said nonwoven fabric.

In the article of the invention arranged as described above, the composite sheets striped with the plastic film are readily folded along the stripes and partial lengths of the crotch side edges of the wearer's shorts along which the respective wings are to be folded back can be considered as segments of straight line. Accordingly, the composite sheets may be positioned at the crotch side edges of the wearer's shorts to facilitate the wings to be folded back accurately along the crotch side edges of the wearer's shorts.

PREFERRED EMBODIMENTS OF THE INVENTION

Details of a menstruation pad according to the invention will be better understood from the following description of preferred embodiments made in reference with the accompanying drawings.

Figure 1:
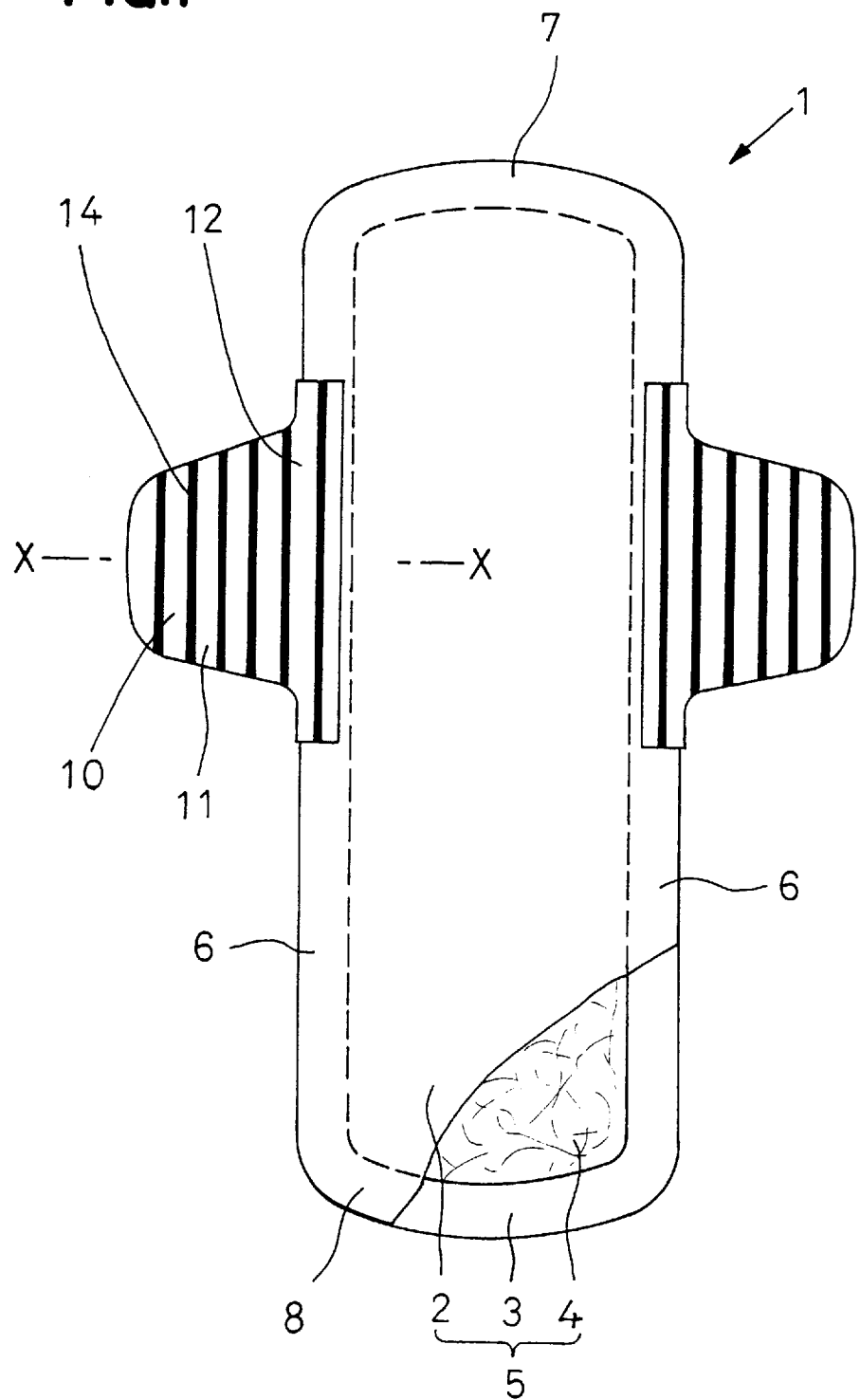
FIG. 1 is a plan view showing an embodiment of a menstruation pad as an absorbent sanitary article arranged according to the invention as partially broken away.
Figure 2:
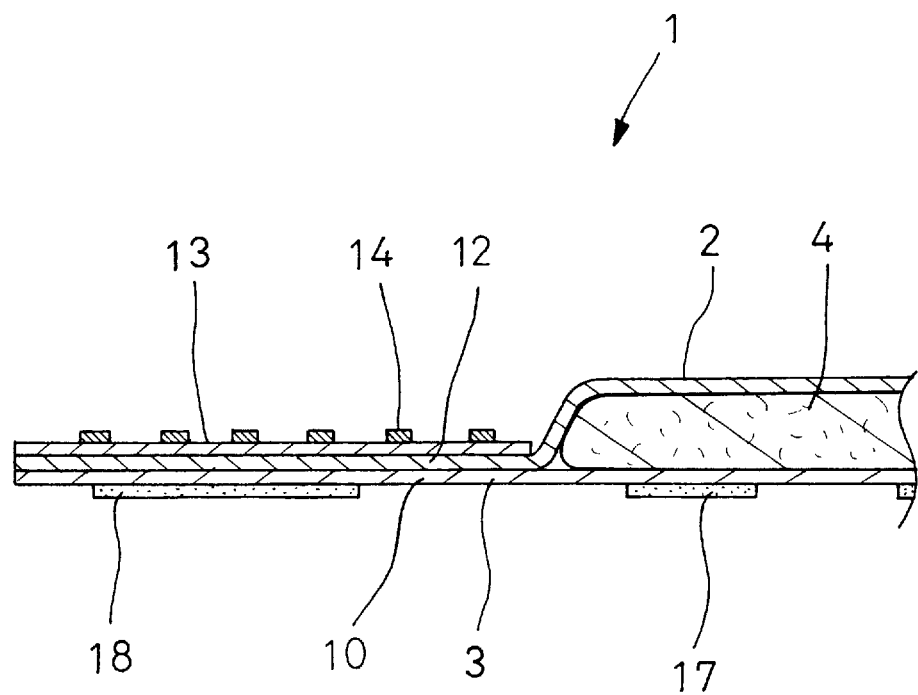
FIG. 2 is a sectional view taken along a line X—X in FIG. 1.

Referring to FIGS. 1 and 2, generally oblong pad 1 has a basic body 5 comprising a liquid-permeable topsheet 2, a liquid-impermeable backsheet 3 and a liquid-absorbent core 4 disposed between these two sheets 2, 3, and portions of the topsheet and backsheet 2, 3 extending outward beyond a peripheral edge of the core 4 are bonded to each other so as to form side flaps 6 in transversely opposite sides and end flaps 7, 8 in longitudinally opposite ends of the pad 1. The pad 1 further comprises a pair of wings 10 extending further outward beyond the respective side flaps 6 at locations thereon nearer to longitudinally front ends of these side flaps 6.

Each of the wings 10 comprises said portions of the topsheet and backsheet 2, 3 extending outward beyond the associated side flaps 6 and bonded to each other, and a composite sheet 11 bonded to the upper surface of the topsheet 2. Each of the composite sheets 11 participates at least in formation of the base end 12 and a portion in the proximity thereof in each wing 10. It should understood that the composite sheet 11 is shown as covering the entire wing 10 and a part of the side flaps 6.

The composite sheet 11 comprises a nonwoven fabric 13 striped with plurality of strips 14 of soft plastic film extending longitudinally of the pad 1 and bonded to the upper surface of the nonwoven fabric 13. The nonwoven fabric 13 preferably has a weight per unit area of 10 to 100 g/m² and is preferably of soft nature. The nonwoven fabric 13 may be made from natural fibers, artificial fibers, synthetic fibers or a mixture thereof. The strips 14 are 5 to 100 µm thick, 0.3 to 7 mm wide, spaced one from another by 0.3 to 7 mm and extend in parallel to one another longitudinally of the pad 1. Such composite sheet 11 is easily folded linearly along one of the strips 14 in a portion of the nonwoven fabric 13 exposed between each pair of adjacent strips 14 and therefore the wing 10 can be linearly folded along the base end 12 of this wing 10 or a line adjacent the base end 12 so far as the composite sheet 11 is provided so as to cover the base end 12 of the wing 10 or said line adjacent the base end 12. In other words, whenever the pad 1 is put on the wearer with the base ends substantially overlying the respective crotch side edges of the wearer's shorts, the wings 10 can be folded accurately along the portions of said crotch side edges which can be considered substantially as segments of straight line. It should be understood that, if said base ends do not overlie said crotch side edges, depending on the size of the wearer's shorts, the wearer will be able to overcome this inconvenience by selecting the pad 1 having the wings 11 completely covered with the composite sheets 11 as in the embodiments shown by the attached drawings.

Arrangement of the wing 10 is not limited to the embodiment shown by the accompanying drawings. For example, it is possible without departing from the scope of the invention to assemble the wing 10 from the composite sheet 11 and any one of the topsheet and backsheet 2, 3 or even from the composite sheet 11 alone. It is also possible to provide the composite sheet 11 on the lower side of the pad 1.

Figure 3:
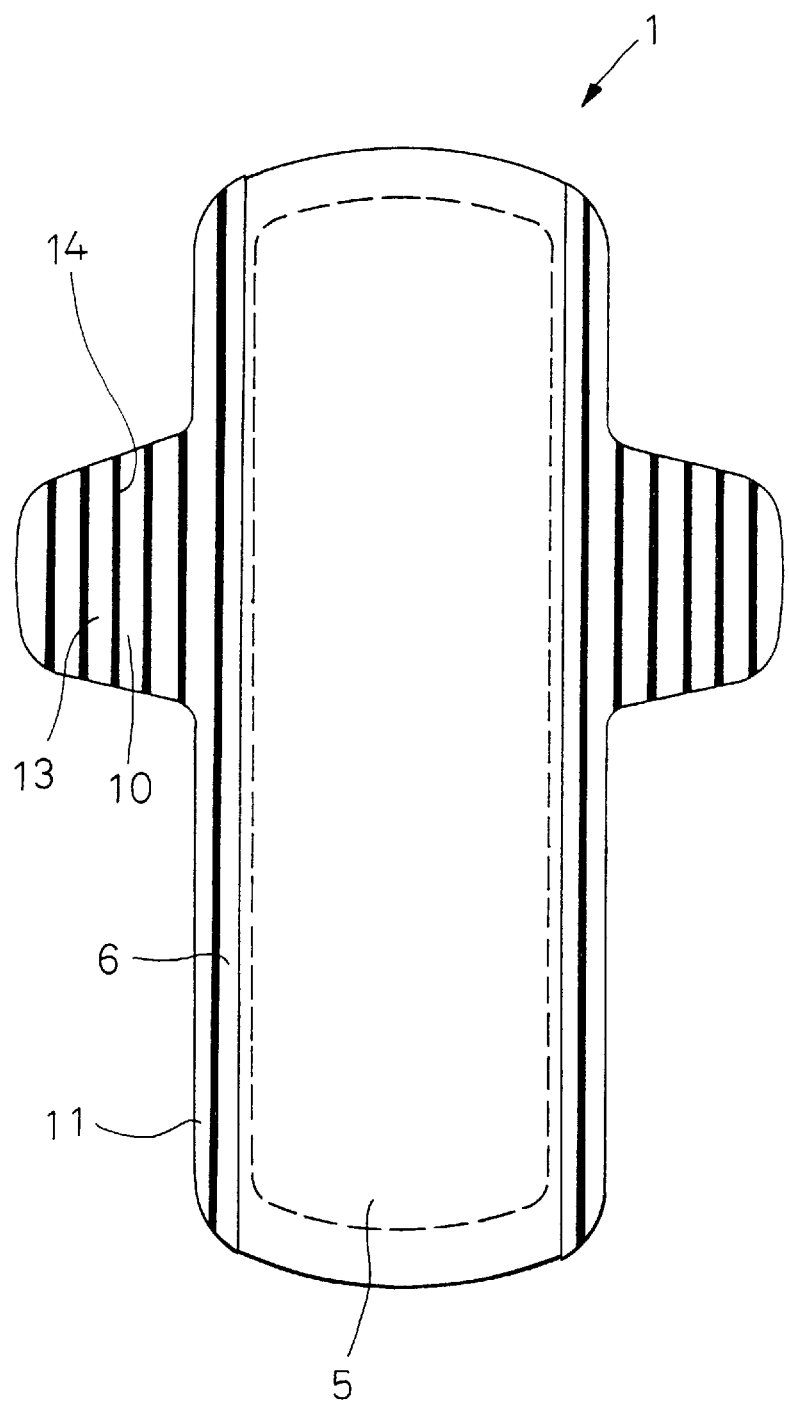
FIG. 3 is a plan view showing the pad embodied differently from that shown by FIG. 1.

Referring to FIG. 3, the composite sheets 11 cover the respective side flaps 6 of the basic body 5 along their longitudinally full extents. When the crotch zone of the wearer's shorts is relatively narrow and it is forced to fold the wings 10 in the areas of the respective side flaps 6, the side flaps 6 embodied as shown by the drawings are convenient to be folded in said areas. The side flaps 6 shown are advantageous also in that, even when menstrual discharge flows transversely from the basic body 5 into the side flaps 6, capillary action of the portions of the nonwoven fabric 13 exposed between the respective pairs of adjacent strips 14 controls said flow of menstrual discharge to spread longitudinally of the pad 1 and thereby prevents menstrual discharge from sideways leakage. To achieve this effect, the nonwoven fabric 13 preferably has appropriate hydrophile property.

Figure 5:
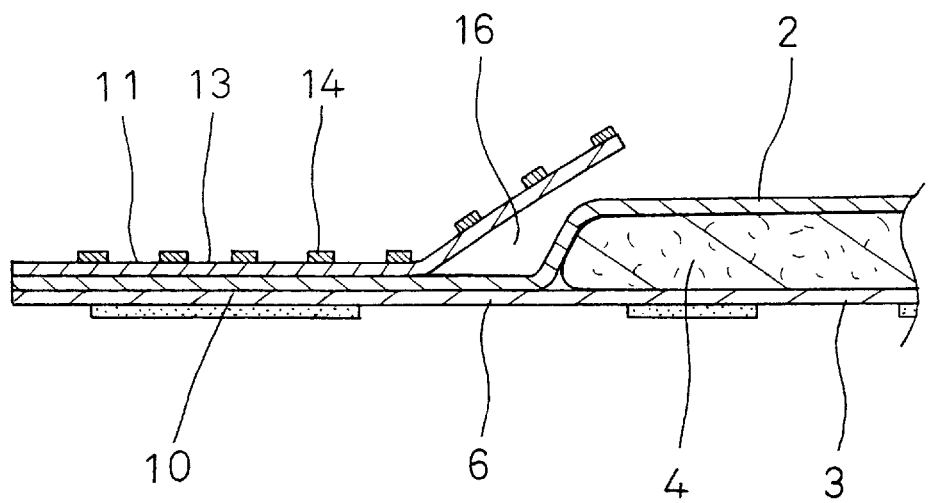
FIG. 5 is a sectional view taken along a line Y—Y in FIG. 4.
Figure 4:
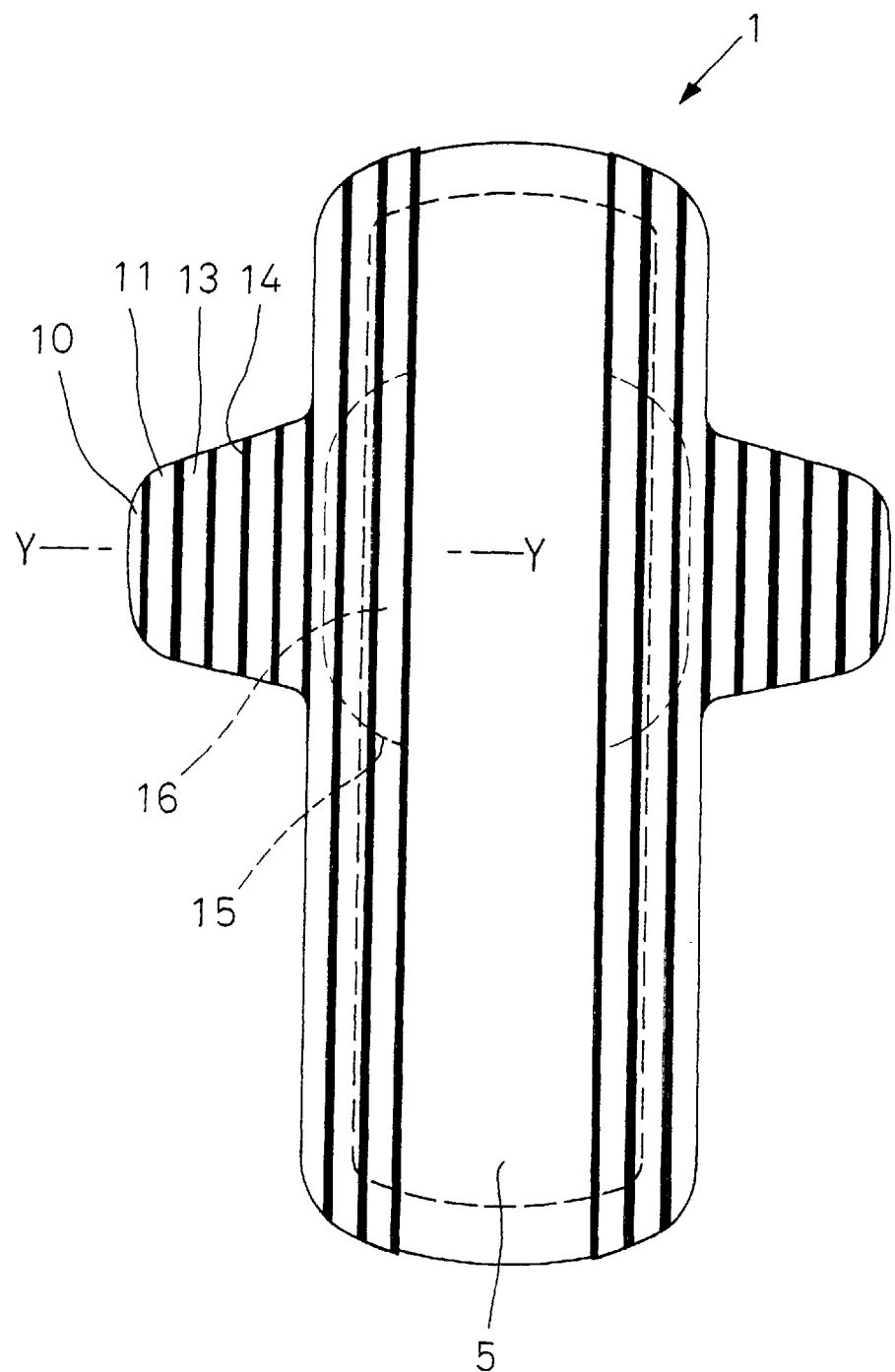
FIG. 4 is a plan view showing the pad embodied differently from those shown by FIGS. 1 and 3.

Referring to FIGS. 4 and 5, the composite sheet 11 is not bonded to the topsheet 2, specifically, in laterally opposite inner side areas of the composite sheet between the base ends of the wings 6 within a central zone defined by a broken line 15, so that the composite sheet 11 may cooperate with the topsheet 2 to form a pocket 16 adapted to be opened toward the center of the pad 1 and thereby to receive any quantity of menstrual discharge flowing sideways (FIG. 5). Even if the nonwoven fabric 13 used as the component of the composite sheet 11 is liquid-permeable, the width of the individual strips 14 cut from a suitable liquid-impermeable plastic film and the pitch at which these strips 14 are arranged may be appropriately selected to make the composite sheet 11 sufficiently function as a leakage-proof sheet.

Adhesive zones 17, 18 are provided on the lower surfaces of the basic body 5 as well as the wings 10 so that the pad 1 may be reliably fastened to the wearer's shorts (FIG. 2). The topsheet and backsheet 2, 3 and the liquid-absorbent core 4 may be made from the materials usually used for such members in this field of art and bonding of the respective members to be assembled into the pad 1 may be performed not only by adhesive bonding technique using hot melt adhesive or the like but also by welding technique, depending on the materials used.

The improved pad of the invention facilitates the wings to be folded accurately along the crotch side edges of the wearer's shorts, since each of the wings includes the composite sheet comprising the nonwoven fabric striped with the strips of plastic film bonded to the upper surface of the nonwoven fabric.

What is claimed is:

1. An absorbent sanitary article comprising a basic body including a liquid-permeable topsheet, a liquid-impermeable backsheet, said topsheet having a periphery secured to the backsheet, and a liquid-absorbent core disposed between, said topsheet and said backsheet, and further including a pair of wings extending laterally outwardly from transversely opposite sides of said basic body, wherein each of said wings is at least partially made of a composite sheet comprising a nonwoven fabric striped with a plurality of at least three strips of plastic film spaced apart from each other and extending substantially parallel to one another longitudinally of said article and bonded to an upper surface of said nonwoven fabric.

2. The absorbent sanitary article according to claim 1, wherein said composite sheets are provided so as to cover at least base ends and areas adjacent said base ends of the respective wings.

3. The absorbent sanitary article according to claim 1, further comprising a pair of side flaps extending longitudinally along the transversely opposite sides of said basic body; wherein said wings extend outwardly from said side flaps; and wherein said composite sheets cover the associated side flaps as well as the associated wings.

4. The absorbent sanitary article according to claim 1, wherein said article is a menstruation pad and sanitary napkin.

5. The absorbent sanitary article according to claim 3, wherein said composite sheet is not bonded to said topsheet at laterally opposite inner side areas of said composite sheet between base ends of said wings; and wherein a pocket is formed by said composite sheet cooperating with said topsheet.

\* \* \* \* \*